United States Patent [19]

Furuuchi et al.

[11] Patent Number: 4,582,635

[45] Date of Patent: Apr. 15, 1986

[54] PERFUME-CONTAINING RESIN

[75] Inventors: Shigemasa Furuuchi, Kanagawa; Shigehiro Katsuragi, Tokyo; Kiyohito Sawano, Kanagawa, all of Japan

[73] Assignees: Takasago Perfumery Co., Ltd.; Asahi Glass Co., Ltd., both of Tokyo, Japan

[21] Appl. No.: 579,582

[22] Filed: Feb. 13, 1984

[30] Foreign Application Priority Data

Feb. 22, 1983 [JP] Japan .................................. 58-27036

[51] Int. Cl.$^4$ ............................ A61K 7/46; C08J 3/20; C08L 31/00
[52] U.S. Cl. ................................ 252/522 A; 424/76; 239/54
[58] Field of Search ..................... 252/522 A; 424/76; 239/54

[56] References Cited

U.S. PATENT DOCUMENTS 4,138,344 2/1979 Choi et al. .................. 252/522 A X

FOREIGN PATENT DOCUMENTS 2010858 7/1979 United Kingdom .
2061308 5/1980 United Kingdom .
2138006 10/1984 United Kingdom ............ 252/522 R Primary Examiner—Thomas A. Waltz
Attorney, Agent, or Firm—Oblon, Fisher, Spivak, McClelland & Maier

[57] ABSTRACT

A perfume-containing resin which is produced by polymerizing diethylene glycol bis(allyl carbonate) in the presence of a perfume. The resin emits a well-balanced fragrance over a long period of time.

14 Claims, 1 Drawing Figure

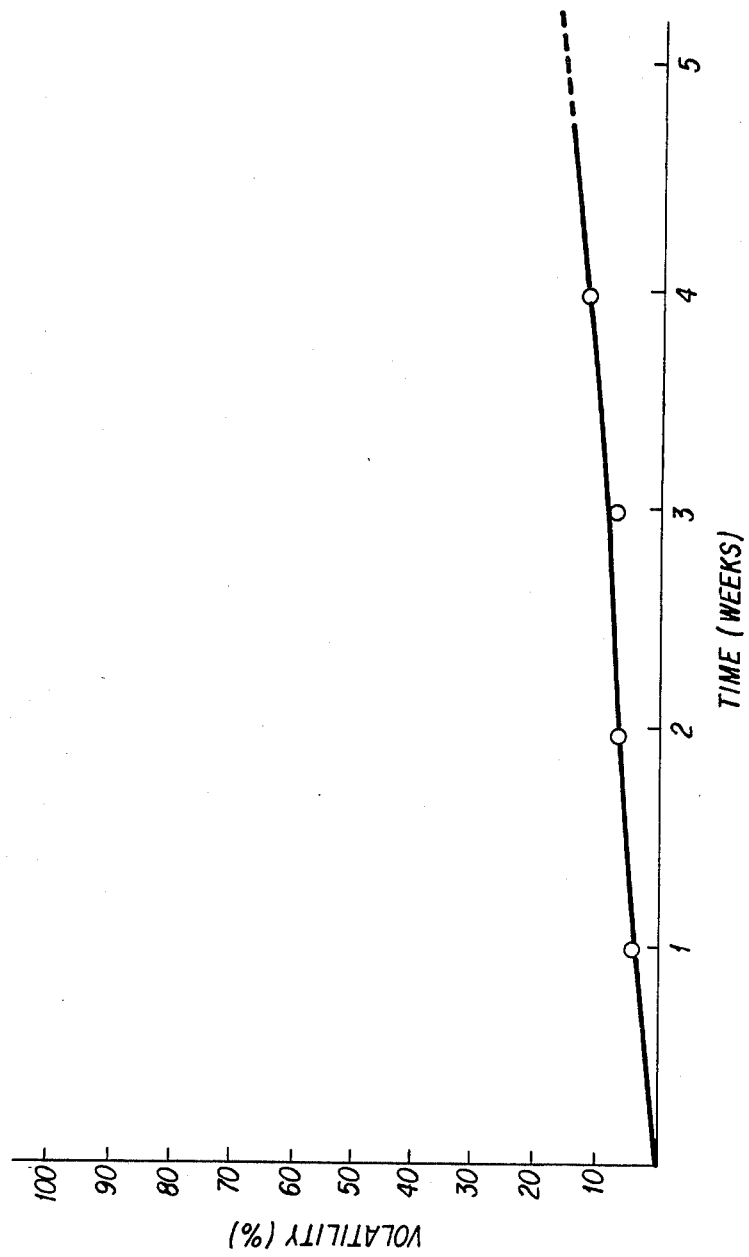

PERFUME-CONTAINING RESIN

FIELD OF THE INVENTION

The present invention relates to a perfume-containing resin which is produced by polymerizing diethylene glycol bis(allyl carbonate) in the presence of a perfume. The perfume-containing resin emits a well-balanced fragrance over a long period of time.

BACKGROUND OF THE INVENTION

Heretofore, the air freshners or odorants have been available in the form of aerosol, gel, liquid, powder, and synthetic resin product. Many attempts have been made to incorporate a perfume into a synthetic resin. However, effective air freshners or odorants cannot be made by such a simple incorporation, because a perfume and a synthetic resin are not compatible with each other and the perfume incorporated into the resin seeps through and rapidly wastes from the surface of the resin, or the perfume is sealed inside the resin and does not diffuse to the surface of the resin. For example, thermoplastic resins of linear hydrocarbons such as polyethylene and polypropylene have a poor gas permeability, whereas polystyrene resin and polyvinyl acetate resin are excessively permeable to a gas. Thus, those materials are not suitable as a substrate for air freshners or odorants.

Several methods have been proposed to overcome these disadvantages of synthetic resin products; a method comprising supporting a hydrophylic polymer of hydrophylic acrylate or methacrylate on a fragrant substance, a method comprising using a chlorinated product of a polyethylene or polyethylene copolymer, a method comprising mixing and melting a perfume into a low molecular weight polyolefin resin and incorporating the resulting pellets into a high molecular weight polyolefin resin, and method comprising mixing a perfume with or impregnating and absorbing a perfume into an ethylene-acrylate ester copolymer or copolymers of ethylene and various acrylic acid esters. However, in some applications of air freshners or ordorants, special properties such as hardness, clarity, and colorability are required.

SUMMARY OF THE INVENTION

As a result of extensive investigations to develop air freshners or odorants which emit a well-balanced fracrance uniformly over a long period of time and have some characteristic properties, it was found that this object can be achieved by a polymer of diethylene glycol bis(allyl carbonate), into which a perfume is incorporated.

Accordingly, an object of this invention is to provide a perfume-containing resin which is produced by polymerizing diethylene glycol bis(allyl carbonate) in the presence of a perfume.

BRIEF DESCRIPTION OF THE ACCOMPANYING DRAWING

The FIGURE is a graph showing the change on the volatility (%) of the perfume used in Example 122 with the passage of time.

DETAILED DESCRIPTION OF THE INVENTION

Diethylene glycol bis(allyl carbonate) used in this invention is a commercially available product, CR-39 (PPG Industries, Inc., U.S.A.). The polymer thereof is an organic glass having optical characteristics and is widely used as spectacles lenses due to its superior properties such as lightness, impact resistance (safety), processability, and dyeability, as compared with an inorganic glass.

According to the embodiment of this invention, a polymerization initiator is added to diethylene glycol bis(allyl carbonate) and then a perfume is well mixed therein. The resulting mixture is cast into a mold of desired shape and uniformly polymerized therein at a prescribed temperature. The polymerization (curing) is conducted at 5° to 100° C. for 1 to 100 hours, preferably at 45° to 50° C. for 5 to 10 hours, and then further conducted at 85° to 90° C. for 3 to 10 hours.

In commercial scale production a mixture of diethylene glycol bis(allyl carbonate), a polymerization initiator, and a perfume is cast into a mold constructed by a glass mold and a synthetic resin gasket and then cured by the method of heating. Curing may also be conducted by adding a photopolymerizing catalyst using a method such as irradiating with an ultraviolet ray lamp, irradiating with a mercury lamp, etc. After polymerization is completed, the perfume-containing resin is taken out from the mold.

The diethylene glycol bis(allyl carbonate) monomer may be copolymerized with at least one of other polymerizable monomers such as diallyl phthalate, benzylmethacrylate, methacrylate, diallyl maleate, diallyl fumarate, diallyl succinate, diallyl crotonate, diallyl benzoate, and diallyl diglycol ester, as disclosed in Unexamined Published Japanese Patent Application No. 61411/1981, to obtain a multicomponent polymer. The amount of the other polymerizable comonomer is preferably 50 wt% or less based on the weight of the diethylene glycol bis(allyl carbonate). Further, a flame retardant, UV absorber, weathering agent, antistatic agent, colorant (such as dyestuff), and the like, can be added.

The polymerization initiator which can be used includes diisopropyl peroxydicarbonate di-sec-butyl peroxydicarbonate, lauroyl peroxide, and azobisisobutyronitrile. Use of benzoyl peroxide tends to require a long curing.

The amount of the polymerization initiator used is 0.1 to 25 wt%, preferably 1 to 15 wt%, based on the weight of diethyleneglycol bis(allyl carbonate).

The perfume which can be used includes a natural perfume, a synthetic perfume, a synthetic essential oil and a natural essential oil.

Examples of the synthetic perfume include terpenic hydrocarbons, esters, ethers, alcohols, aldehydes, phenols, ketons, acetals, oximes and mixtures thereof.

Examples of the terpenic hydrocarbons include lime terpene, lemon terpene and limonen dimer.

Examples of the esters include γ-undecalactone, ethyl methyl phenyl glycidate, allyl caproate, amyl salicylate, amyl benzoate, amyl acetate, benzyl acetate, benzyl benzoate, benzyl salicylate, benzyl propionate, butyl acetate, benzyl butyrate, benzyl phenylacetate, cedryl acetate, citronellyl acetate, citronellyl formate, p-cresyl acetate, 2-t-pentyl-cyclohexyl acetate, cyclohexyl acetate, cis-3-hexenyl acetate, cis-3-hexenyl salicylate, dimethylbenzyl acetate, diethyl phthalate, δ-decalactone dibutyl phthalate, ethyl butyrate, ethyl acetate, ethyl benzoate, fenchyl acetate, geranyl acetate, γ-dodecalatone, methyl dihydrojasmonate, isobornyl acetate, β-isopropoxyethyl salicylate, linalyl acetate, methyl benzoate, o-t-buthylcylohexyl acetate, methyl salicylate, ethylene brassylate, ethylene dodecanoate, methyl phenyl acetate, nopyl acetate, phenylethyl isobutyrate, phenylethylphenyl acetate, phenylethyl acetate, methyl phenyl carbinyl acetate, 3,5,5-trimethylhexyl acetate, terpinyl acetate, triethyl citrate, p-t-butylcyclohexyl acetate and vetiver acetate.

Examples of the ethers include p-cresyl methyl ether, diphenyl ether, 1,3,4,6,7,8-hexahydro-4,6,7,8,8-hyxamethyl cyclopenta-γ-2-benzopyran and phenyl isoamyl ether.

Examples of the alcohols include n-octyl alcohol, n-nonyl alcohol, β-phenylethyldimethyl carbinol, dimethyl benzyl carbinol, carbitol dihydromyrcenol, dimethyl octanol, hexylene glycol linalool, leaf alcohol, nerol, phenoxyethanol, γ-phenylpropyl alcohol, β-phenylethyl alcohol, methylphenyl carbinol, terpineol, tetrahydroalloocimenol, tetrahydrolinalool and 9-decen-1-ol.

Examples of the aldehydes include n-nonyl aldehyde, undecylene aldehyde, methylnonyl acetaldehyde, anisaldehyde, benzaldehyde, cyclamenaldehyde, 2-hexylhexanal, α-hexylcinnamic aldehyde, phenyl acetaldehyde, 4-(4-hydroxy-4-methylpentyl)-3-cyclohexene-1-carboxyaldehyde, p-t-butyl-α-methylhydrocinnamic aldehyde, hydroxycitronellal, α-amylcinnamic aldehyde and 3,5-dimethyl-3-cyclohexene-1-carboxyaldehyde.

Examples of the phenols include methyl eugenol.

Examples of the ketones include l-carvone, α-damascon, ionone, 4-t-pentylcyclohexanone, 3-amyl-4-acetoxytetrahydropyran, menthone, methylionone, p-t-amycyclohexanone and acetyl cedrene.

Examples of the acetals include phenylacetaldehydedimethyl acetal.

Examples of the oximes include 5-methyl-3-heptanon oxime.

The perfume can be used alone or as mixtures thereof.

The amount of the perfume added is 1 to 60 wt%, preferably 5 to 45 wt%, based on the weight of the diethylene glycol bis(allyl carbonate). If the amount of perfume is too small, the life as the air freshners or odorants is short and the commercial value thereof is lost. If the amount of perfume is too large, the curing time becomes long, so that the productivity is reduced, the product obtained is soft due to insufficient polymerization, or cracking occurs on the product.

The perfume-containing resin is greatly influenced depending upon the type of perfume used such that the inherent fragrance of a perfume changes, a resin which is inherently colorless and transparent shows coloration or the hardness of a resin is adversely affected. Therefore, the perfume used must be carefully selected according to the purpose of use of the perfume containing resin.

Regarding the influence of the perfume to the resin, there is no perfume showing a remarkable change of the fragrance, but as explained in the following Examples, a relatively low boiling perfume, particularly benzaldehyde and ethyl acetate, shows the change of fragrance and the intensity of fragrance is decreased.

Examples of the perfumes which tend to color a colorless and transparent resins in light yellow, include n-nonylaldehyde, methylnonylacetaldehyde, benzaldehyde, cyclamenaldehyde, citral, cinnamic aldehyde, cedryl acetate, eugenol, isoeugenol, methyl eugenol, cis-jasmone, l-carvone, γ-methyl ionone, methyl dihydrojasmonate, α-hexylcinnamic aldehyde, phenylacetoaldehyde, 4-t-phenylcyclohexanone, hydroxycitronellal, methyl anthranilate, α-amyl cinnamic aldehyde, 5-methyl-3-pentanoneoxime, vetiver aldehyde, acetyl cedrene, limonene dimer, etc. Of these perfumes, the perfumes which have the particularly strong coloration tendency, are cinnamic aldehyde, α-amylcinnamic aldehyde and α-hexylcinnamic aldehyde which have a double bond conjugated with the aromatic nucleus and an aldehyde group; eugenol which is a phenol derivative; methyl anthranilate which is a nitrile or nitrogen-containing compound; and 5-methyl-3-heptanoneoxime.

The perfumes which tend to lower the hardness of the resin and cause the cured resin to remain in the liquid or gell state include cinnamic alcohol, citronellal, citral, citronellol, caryophyllene, cedrene, Cedar H (a product of Takasago Corporation), cinnamic aldehyde, cinnamyl acetate, cis-jasmone, eugenol, isoeugenol, and methyl anthranilate. Of these perfumes, the perfumes which particularly affect the curing, whereby the polymer is not solidified and remains in the liquid state are cinnamic alcohol, citral, caryophyllene, Cedar H (a product of Takasago Corporation), cinnamic aldehyde, cinnamyl acetate, eugenol, isoeugenol, and methyl anthranilate.

Therefore, for example, to the resins having the purpose of use which requires colorless, transparent and hard properties, use of a perfume which impairs these properties, for example, cinnamic aldehyde, should be avoided.

The perfume-containing resin prepared as described above emits the perfume slowly and uniformly over a long period of time and has excellent characteristics as air freshners or odorants. Further, the inherent characteristics of the resin such as transparency, easy coloration with dye and excellent hardness are not deteriorated. Thus, the perfume-containing resin has a wide use as a base material for pendants, brooches, buttons, cuff links, tiepins and other personal ornaments; room ornaments; desk lamp shade; furniture knobs and pulls; key holders; sunglasses (spectacle lenses); mirrors; telephone sets; flower vases; rulers, cardboards (laid under writing paper) and other writing materials; and air freshners or odorants for cars and bathrooms.

The invention is now described in detail by reference to the following examples.

EXAMPLES 1 TO 121

A 10 ml cylindrical glass bottle was filled in a volume of ¾ with diethylene glycol bis(allyl carbonate) containing 4 wt% of diisopropyl peroxydicarbonate as a polymerization initiator. A single perfume was then added to the glass bottle and well mixed. The glass bottle was completely filed with diethylene glycol bis(allyl carbonate), followed by shaking for thorough mixing. The bottle was covered and placed in an oven to polymerize by heating. The heating conditions were as follows:

Examples 1 to 33: Heating at 45° to 50° C. for 5 hours, gradually increasing the temperature to 90° C. over 2 hours, and then heating at 90° to 95° C. for 11 hours.

Examples 34 to 69: Heating at 40° to 45° C. for 7 hours, gradually increasing the temperature to 90° C. over 4 hours, and then heating at 90° to 95° C. for 13 hours.

Examples 70 to 121: Heating at 40° to 45° C. for 7 hours, gradually increasing the temperature to 90° C. over 1 hour, and then heating at 90° to 95° C. for 11 hours.

After polymerization was completed, the bottle was cooled to room temperature and the resulting resin was observed. The solidified resin was separated from the bottle by breaking the bottle. The results obtained are shown in Table 1 below.

Symbols used in Table 1 have the following meanings.

(1) Degree of Coloration of Resin:
"−": No coloration
"+": Slight coloration
"++": Apparent coloration (2) Change in Fragrance of Perfume
"−": No change
"+": Slightly noticeable change
"++": Apparently noticeable change (3) Degree of Hardness of Resin Obtained:
⊙ : Hard to the touch
○ : Slightly hard to the touch
Δ: Soft to the touch
X: Very soft in the form of gell
XX: Liquid (not solidified)

TABLE 1

| Example No. | Perfume Used | Amount of Perfume g | Amount of Diethylene Glycol Bis (allyl) Carbonate g | Change in Color | Change in Fragrance of Perfume | Hardness of Resin |
|---|---|---|---|---|---|---|
| 1 | n-Octyl alcohol | 1.40 | 13.68 | − | − | ⊙ |
| 2 | n-Nonyl alcohol | 1.53 | 13.19 | − | − | ⊙ |
| 3 | n-Nonyl Aldehyde | 1.44 | 12.20 | + | − | ⊙ |
| 4 | Undecylene aldehyde | 1.32 | 11.89 | − | − | ⊙ |
| 5 | Methyl nonyl acetaldehyde | 1.44 | 11.43 | + | − | ⊙ |
| 6 | γ-Undecalactone | 1.58 | 11.97 | − | − | ⊙ |
| 7 | Ethyl methyl-phenylglycidate | 1.46 | 11.50 | − | − | ⊙ |
| 8 | Allyl caproate | 1.60 | 12.21 | − | − | ○ |
| 9 | Amyl salicylate | 1.21 | 10.70 | − | − | ⊙ |
| 10 | Acetophenone | 1.27 | 11.86 | − | − | |
| 11 | Amyl benzoate | 1.29 | 10.57 | − | − | ⊙ |
| 12 | Amyl acetate | 1.34 | 12.64 | − | − | ⊙ |
| 13 | Anisaldehyde | 1.27 | 13.65 | − | − | ⊙ |
| 14 | Benzyl acetate | 1.45 | 12.28 | − | − | ⊙ |
| 15 | Benzyl benzoate | 1.22 | 12.32 | − | − | ⊙ |
| 16 | Benzaldehyde | 1.39 | 10.77 | + | + | ⊙ |
| 17 | Benzyl salicylate | 1.70 | 11.88 | − | − | ⊙ |
| 18 | Benzyl propionate | 1.30 | 12.03 | − | − | ⊙ |
| 19 | Butyl acetate | 1.19 | 11.78 | − | − | ⊙ |
| 20 | β-Phenylethyl dimethyl carbinyl | 1.71 | 11.32 | − | − | ⊙ |
| 21 | Benzyl butyrate | 1.60 | 12.03 | − | − | ⊙ |
| 22 | Benzyl phenylacetate | 1.23 | 10.25 | − | − | ⊙ |
| 23 | Cinnamic alcohol | 1.33 | 13.71 | − | − | XX |
| 24 | Citronellal | 1.30 | 11.11 | − | − | X |
| 25 | Citral | 1.50 | 11.90 | + | − | XX |
| 26 | Cyclamen aldehyde | 1.34 | 13.26 | + | − | ⊙ |
| 27 | Cedryl acetate | 1.23 | 11.49 | + | − | ⊙ |
| 28 | p-Cresyl methyl ether | 1.30 | 11.81 | − | − | ⊙ |
| 29 | Citronellol | 1.34 | 12.76 | − | − | X |
| 30 | Citronellyl acetate | 1.21 | 11.30 | − | − | ⊙ |
| 31 | Carylophylene | 1.40 | 11.02 | − | − | XX |
| 32 | Cedrene | 1.29 | 11.51 | − | − | X |
| 33 | Cedar H (a product of Takasago Corporation) | 1.39 | 11.39 | − | − | XX |
| 34 | Cinnamic aldehyde | 1.25 | 13.15 | ++ | − | XX |
| 35 | Cinnamyl acetate | 1.64 | 11.71 | − | − | XX |
| 36 | Cis-jasmone | 1.32 | 13.46 | + | − | X |
| 37 | Citronellyl formate | 1.27 | 13.09 | − | − | ⊙ |
| 38 | Carbitol | 1.25 | 13.29 | − | − | ⊙ |
| 39 | p-Cresyl acetate | 1.17 | 13.14 | − | − | ⊙ |
| 40 | l-Carvone | 1.16 | 13.03 | + | − | ○ |
| 41 | 2-t-Pentyl-cyclohexyl acetate | 1.23 | 12.55 | − | − | ⊙ |
| 42 | Cyclohexyl acetate | 1.12 | 13.49 | − | − | ⊙ |
| 43 | Cis-3-hexenyl acetate | 1.16 | 13.48 | − | − | ⊙ |

TABLE 1-continued

| Example No. | Perfume Used | Amount of Perfume g | Amount of Diethylene Glycol Bis (allyl Carbonate g | Change in Color | Change in Fragrance of Perfume | Hardness of Resin |
|---|---|---|---|---|---|---|
| 44 | Cis-3-hexenyl salicylate | 1.32 | 13.75 | — | — | ◎ |
| 45 | α-Damascon | 1.25 | 13.88 | — | — | O |
| 46 | Dimethylbenzyl acetate | 1.30 | 13.54 | — | — | ◎ |
| 47 | Diethyl phthalate | 1.35 | 13.50 | — | — | ◎ |
| 48 | Diphenyl ether | 1.30 | 12.87 | — | — | ◎ |
| 49 | Dimethyl benzyl carbinol | 1.31 | 12.71 | — | — | ◎ |
| 50 | Dihydromyrcenol | 1.16 | 13.97 | — | — | ◎ |
| 51 | Dimethyl octanol | 1.26 | 12.72 | — | — | ◎ |
| 52 | δ-Decalactone | 1.41 | 14.38 | — | — | ◎ |
| 53 | Dibutyl phthalate | 1.36 | 13.20 | — | — | ◎ |
| 54 | Eugenol | 1.15 | 14.02 | ++ | — | XX |
| 55 | Ethyl butyrate | 1.20 | 12.76 | — | — | ◎ |
| 56 | Ethyl acetate | 1.20 | 13.48 | — | ++ | |
| 57 | Ethyl benzoate | 1.12 | 14.35 | — | — | ◎ |
| 58 | Fenchyl acetate | 1.13 | 14.12 | — | — | ◎ |
| 59 | 1,3,4,6,7,8-Hexahydro-4,6,7,8,8-hexamethyl-cyclopenta-γ-2-benzopyran | 1.39 | 13.62 | — | — | ◎ |
| 60 | Geraniol | 1.24 | 12.78 | — | — | Δ |
| 61 | Geranyl acetate | 1.21 | 13.59 | — | — | O |
| 62 | γ-Methyl ionone | 1.20 | 14.11 | + | — | Δ |
| 63 | 2-Hexylhexanal | 1.37 | 14.12 | — | — | O |
| 64 | γ-Dodecalactone | 1.36 | 13.20 | — | — | |
| 65 | Methyldihydojasmonate | 1.25 | 13.44 | + | — | O |
| 66 | α-Hexylcinnamic aldehyde | 1.19 | 12.93 | ++ | — | O |
| 67 | Phenylacetaldehyde dimethylacetal | 1.36 | 13.07 | — | — | ◎ |
| 68 | Phenylacetaldehyde | 1.16 | 12.74 | + | — | O |
| 69 | Hexylene glycol | 1.27 | 12.70 | — | — | O |
| 70 | Isobornyl acetate | 1.29 | 13.03 | — | — | ◎ |
| 71 | Ionone | 1.40 | 12.96 | — | — | O |
| 72 | 4-t-Pentyl-cyclohexanone | 1.34 | 12.18 | + | — | |
| 73 | Isoeugenol | 1.53 | 15.00 | + | — | XX |
| 74 | β-Isopropoxy-ethyl salicylate | 1.43 | 11.62 | — | — | ◎ |
| 75 | 3-Amyl-4 acetoxytetrahydropyran | 1.21 | 12.87 | — | — | ◎ |
| 76 | Mixture of nonandiol diacetate and 3-amyl-4-acetoxytetrahydropyran | 1.42 | 13.27 | — | — | ◎ |
| 77 | 4-(4-Hydroxy-4-methylpentyl)-3-cyclohexene-1-carboxyaldehyde | 1.25 | 14.70 | — | — | ◎ |
| 78 | p-t-Butyl-α-methylhydrocinnamic aldehyde | 1.31 | 13.36 | — | — | ◎ |
| 79 | Hydroxy citronellal | 1.52 | 15.20 | + | — | ◎ |
| 80 | Linalool | 1.27 | 10.94 | — | — | ◎ |
| 81 | Leaf Alcohol | 1.28 | 11.63 | — | — | |
| 82 | Linalyl acetate | 1.27 | 13.65 | — | — | |
| 83 | Lime terpene | 1.22 | 13.26 | — | — | O |
| 84 | Lemon terpene | 1.53 | 16.63 | — | — | O |
| 85 | Methyl benzoate | 1.23 | 12.94 | — | — | ◎ |
| 86 | Methyl | 1.49 | 12.95 | ++ | — | XX |

TABLE 1-continued

| Example No. | Perfume Used | Amount of Perfume g | Amount of Diethylene Glycol Bis (allyl) Carbonate g | Change in Color | Change in Fragrance of Perfume | Hardness of Resin |
|---|---|---|---|---|---|---|
| | anthranilate | | | | | |
| 87 | o-t-Butyl-cyclohexyl acetate | 1.28 | 13.61 | — | — | ◎ |
| 88 | Menthone | 1.31 | 13.10 | — | — | ◎ |
| 89 | Methyl ionone | 1.30 | 12.26 | — | — | O |
| 90 | Methyl eugenol | 1.33 | 15.28 | + | — | O |
| 91 | Methyl salicylate | 1.22 | 13.40 | — | — | ◎ |
| 92 | Ethylene brassylate | 1.25 | 12.75 | — | — | ◎ |
| 93 | Ethylene dodecanoate | 1.55 | 13.36 | — | — | ◎ |
| 94 | Methyl phenylacetate | 1.28 | 14.66 | — | — | ◎ |
| 95 | Nerol | 1.34 | 13.95 | — | — | O |
| 96 | Nopyl acetate | 1.40 | 13.46 | — | — | ◎ |
| 97 | Nacintha (naarden INT NV) | 1.28 | 13.33 | — | — | ◎ |
| 98 | α-Amylcinnamic aldehyde | 1.30 | 12.62 | ++ | — | O |
| 99 | p-t-Amylcyclo-hexanone | 1.31 | 13.64 | — | — | ◎ |
| 100 | Phenylethyl isobutyrate | 1.30 | 13.68 | — | — | ◎ |
| 101 | Phenylethyl phenylacetate | 1.29 | 12.40 | — | — | ◎ |
| 102 | β-Phenoxyethanol | 1.18 | 12.16 | — | — | ◎ |
| 103 | γ-Phenylpropyl alcohol | 1.30 | 11.81 | — | — | ◎ |
| 104 | Phenylethyl acetate | 1.28 | 15.05 | — | — | ◎ |
| 105 | β-Phenylethyl alcohol | 1.40 | 12.84 | — | — | ◎ |
| 106 | Methylphenyl-carbinyl acetate | 1.51 | 14.24 | — | — | ◎ |
| 107 | Methylphenyl carbinol | 1.38 | 14.08 | — | — | ◎ |
| 108 | 3,5,5-Trimethyl-hexylacetate | 1.38 | 14.08 | — | — | O |
| 109 | 5-Methyl-3-heptanoneoxime | 1.22 | 12.44 | ++ | — | O |
| 110 | Terpinyl acetate | 1.34 | 13.26 | — | — | O |
| 111 | 3,5-Dimethyl-3-cyclohexene-1-carboxyaldehyde | 1.24 | 14.09 | — | — | O |
| 112 | Terpineol | 1.22 | 12.70 | — | — | O |
| 113 | Tetrahydro-alloocimenol | 1.46 | 12.58 | — | — | O |
| 114 | Tetrahydro-linalool | 1.30 | 12.03 | — | — | O |
| 115 | 9-Decene-1-ol | 1.11 | 11.68 | — | — | ◎ |
| 116 | Phenylisoamyl ether | 1.17 | 13.00 | — | — | ◎ |
| 117 | Triethyl citrate | 1.48 | 13.33 | — | — | ◎ |
| 118 | p-t-Butylcyclo-hexyl acetate | 1.21 | 11.98 | — | — | ◎ |
| 119 | Vetiver acetate | 1.28 | 12.19 | + | — | O |
| 120 | Acetylcedrene | 1.42 | 11.93 | + | — | ◎ |
| 121 | Limonene dimer | 1.22 | 13.40 | + | — | O |

EXAMPLE 122

A compounding perfume having the flavor of strawberry was prepared according to the following recipe.

| | Parts by weight |
|---|---|
| Ethyl butyrate | 20 |
| α-Amylcinnamic aldehyde | 35 |
| γ-Methylionone | 50 |
| Amyl acetate | 30 |
| Methyl benzoate | 5 |

-continued

| | Parts by weight |
|---|---|
| Ethyl methyl phenyl glycidate | 80 |
| γ-Undecalactone | 20 |
| Diethyl phthalate | 600 |
| Allyl caproate | 20 |
| Butyl acetate | 10 |
| Benzyl acetate | 50 |
| Ethylene Brassylate | 10 |
| β-Isopropoxyethyl salicylate | 70 |

31.48 g of diethylene glycol bis(allyl carbonate) containing 4 wt% of diisopropyl peroxydicarbonate as a polymerization initiator was placed in a stainless steel oval mold having a thickness of 5 mm and a volume of 35 ml in volume and 3.50 g of the compounding perfume was added thereto. After thoroughly mixing, the mold was covered and heated in an oven. The temperature was kept at 45° to 50° C. for 7 hours, and then the temperature was gradually increased over 2 hours, followed by heating at 92° to 98° C. for 10 hours. After polymerization was completed, the mold was cooled to room temperature and the molded product was taken out. The molded product had the weight of 34.97 g and was a hard product like a colorless, transparent glass. Five perfumers of long experience for ten years or more made comparison on the fragrance between the compounding perfume initially added and the molded product. As a result, it was all the evaluation that there was no substantial change on the fragrance therebetween.

The molded product was allowed to stand in a chamber having an air flow of 2.5 m/sec and exposed to the air flow to observe the volatility of the perfume. The molded product was weighed every week. The results obtained are shown in Table 2.

TABLE 2

|  | Initial | 1 week | 2 weeks | 3 weeks | 4 weeks |
|---|---|---|---|---|---|
| Weight of molded product (g) | 34.97 | 34.81 | 34.72 | 34.66 | 34.50 |
| Amount of volatized perfume (g) | 0 | 0.16 | 0.25 | 0.31 | 0.47 |
| Volatility of perfume (%) | 0 | 4.5 | 7.1 | 8.8 | 13.4 |

Volatility of perfume (%) = (A/B) × 100 wherein
A is the amount of volatilized perfume and
B is the weight of perfume added initially.

The relationship thereof is shown in the FIGURE. As apparent from the FIGURE, the volatility of perfume is almost linear. This indicates that the perfume volatilizes uniformly. According to the evaluation on the fragrance by the same perfumers every weekend, the initially added compounding perfume did not almost change the fragrance and the molded product kept emitting the fragrance of the compounding perfume over four weeks.

EXAMPLE 123

0.8 g of the compounding perfume prepared in Example 122 and 0.7 g of diisopropyl peroxycarbonate were dissolved in 20 g of diethylene glycol bis(allyl carbonate). The resulting solution was cast into a mold for molding spectacle lenses, the upper and bottom portions of which were sealed with glass molds and the circumference of which was sealed with a plastic gasket sealing the edges of the glass molds. The mold was placed in an oven. The temperature in the oven was maintained at 45° to 50° C. for 8 hours, gradually increased to 90° C. over 8 hours, and then kept at 90° to 95° C. for 2 hours. After polymerization was completed, the mold was cooled to room temperature and the molded product was taken out. The molded product was thoroughly washed with trichloroethylene. The product obtained had a weight of 21.5 g and was colorless, transparent spectacle lens which emits a fracgrance. The lens had a surface hardness of 6 to 8 as measured according to JIS K6911 using a Barcol hardness tester. The lens was dyed by dipping in a dye solution of Mars Orange Lot No. M-122 (made by Asahi Glass Co., Ltd.) at 83° C. for about 8 seconds, so that the lens had a luminous transmittance of 85%. After thorough water washing and drying, the lens was inspected in the same manner as in the ordinary spectacle lenses and the same results as obtained in the ordinary spectacle lenses were obtained. The lenses thus pepared were made into a pair of spectacles. In performance test of the spectacles, the lenses did not cause any practical problem such as slipping off from the frame due to vibrations and temperature change. As to the light resistance, the lenses passed the fadeometer test for 100 hours.

EXAMPLE 124

Production of fragrant pendant:

|  | Parts by weight |
|---|---|
| Benzyl acetate | 500 |
| Methyl dihydrojasmonate | 100 |
| 3-Amyl-4-acetoxytetrahydropyran | 50 |
| Mixture of nonandioldiacetate and 3-Amyl-4-acetoxytetrahydropyran | 50 |
| Methyl benzoate | 5 |
| p-Cresyl methyl ether | 2 |
| Ylang Ylang oil (synthetic) | 30 |
| Jasmin absolute | 10 |
| γ-Undecalactone | 3 |
| γ-Decalactone | 1 |
| Hydroxy citronellol | 20 |
| Leaf alcohol | 1 |
| Civet absolute | 2 |
| Cis-3-Hexenyl acetate | 1 |
| Benzyl benzoate | 225 |
|  | 1000 |

In accordance with the same procedure as in Example 123, 0.6 g of above jasmin-type compounding perfume was incorporated into 15.74 g of diethylene glycol bis(allyl carbonate) containing 4 wt% of diisopropyl peroxy dicarbonate. Thus, a transparent plastic pendant with jasmin fragrance was obtained.

EXAMPLE 125

Production of fragrant flower vase:

|  | Parts by weight |
|---|---|
| Phenylethyl alcohol | 600 |
| Phenylethyl acetate | 20 |
| Rose oil (synthetic) | 10 |
| Diphenyl oxide | 1 |
| Rosephenone | 2 |
| Phenylethyl phenyl acetate | 16 |
| Geranium oil | 2 |
| Palmarosa oil | 20 |
| Undecylenic aldehyde | 2 |
| Rose oxide | 1 |
| Phenylethyl isobutyrate | 30 |
| δ-Undeca lactone | 5 |
| Benzaldehyde | 1 |
| Benzyl benzoate | 290 |
|  | 1000 |

0.85 g of the above rose-type compounding perfume was incorporated into 15.74 g of diethylene glycol bis-(allyl carbonate) containing 4 wt% of diisopropyl peroxy dicarbonate, and cast into a pentagonal pillar mold for molding. Polymerization was performed by heating in an oven at 40°–45° C. for 7 hours, increasing the temperature to 90° C. over 4 hours, and the keeping the temperature at 90°–95° C. for 10 hours. After polymerization was completed, the mold was cooled to room temperature and the molded product was taken out. Thus, a transparent and hard perfume-containing plastic flower vase like glass was obtained.

While the invention has been described in detail and with reference to specific embodiments thereof, it will be apparent to one skilled in the art that various changes and modifications can be made therein without departing from the spirit and scope thereof.

What is claimed is:

1. A perfume-containing resin obtained by polymerizing diethylene glycol bis(allyl carbonate) in the presence of a perfume.

2. A perfume-containing resin as claimed in claim 1, wherein the resin contains a dyestuff.

3. A perfume-containing resin as claimed in claim 1, wherein the amount of the perfume is 1 to 60% by weight based on the weight of diethylene glycol bis(allyl carbonate).

4. A perfume-containing resin as claimed in claim 1, wherein the perfume is selected from the group consisting of a synthetic perfume, a natural perfume, a synthetic essential oil, a natural essential oil and a mixture thereof.

5. A perfume-containing resin as claimed in claim 4, wherein the synthetic perfume is selected from the group consisting of terpenic hydrocarbons, esters, ethers, alcohols, aldehydes, phenols, ketones, acetals, oximes and mixtures thereof.

6. A perfume-containing resin as claimed in claim 5, wherein the terpenic hydrocarbon is selected from the group consisting of lime terpene, lemon terpene and limonen dimer.

7. A perfume-containing resin as claimed in claim 5, wherein the ester is selected from the group consisting of γ-undecalactone, ethyl methyl phenyl glycidate, allyl caproate, amyl salicylate, amyl benzoate, amyl acetate, benzyl acetate, benzyl benzoate, benzyl salicylate, benzyl propionate, butyl acetate, benzyl butyrate, benzyl phenylacetate, cedryl acetate, citronellyl acetate, citronellyl formate, p-cresyl acetate, 2-t-pentyl-cyclohexyl acetate, cyclohexyl acetate, cis-3-hexenyl acetate, cis-3-hexenyl salicylate, dimethylbenzyl acetate, diethyl phthalate, δ-decalactone, dibutyl phthalate, ethyl butyrate, ethyl acetate, ethyl benzoate, fenchyl acetate, geranyl acetate, γ-dodecalatone, methyl dihydrojasmonate, isobornyl acetate, β-isopropoxyethyl salicylate, linalyl acetate, methyl benzoate, o-t-buthylcyclohexyl acetate, methyl salicylate, ethylene brassylate, ethylene dodecanoate, methyl phenyl acetate, nopyl acetate, phenylethyl isobutyrate, phenylethylphenyl acetate, phenylethyl acetate, methyl phenyl carbinyl acetate, 3,5,5-trimethylhexyl acetate, terpinyl acetate, triethyl citrate, p-t-butylcyclohexyl acetate and vetiver acetate.

8. A perfume-containing resin as claimed in claim 5, wherein the ether is selected from the group consisting of p-cresyl methyl ether, diphenyl ether, 1,3,4,6,7,8-hexahydro-4,6,7,8,8-hexamethyl cyclopenta-γ-2-benzopyran and phenyl isoamyl ether.

9. A perfume-containing resin as claimed in claim 5, wherein the alcohol is selected from the group consisting of n-octyl alcohol, n-nonyl alcohol, β-phenylethyldimethyl carbinol, dimethyl benzyl carbinol, carbitol, dihydromyrcenol, dimethyl octanol, hexylene glycol linalool, leaf alcohol, nerol, phenoxyethanol, γ-phenylpropyl alcohol, β-phenylethyl alcohol, methylphenyl carbinol, terpineol, tetrahydroalloocimenol, tetrahydrolinalool and 9-decen-1-ol.

10. A perfume-containing resin as claimed in claim 5, wherein the aldehyde is selected from the group consisting of n-nonyl aldehyde, undecylene aldehyde, methylnonyl acetaldehyde, anisaldehyde, benzaldehyde, cyclamenaldehyde, 2-hexylhexanal, α-hexylcinnamic aldehyde, phenyl acetaldehyde, 4-(4-hydroxy-4-methylpentyl)-3-cyclohexene-1-carboxyaldehyde, p-t-butyl-α-methylhydrocinnamic aldehyde, hydroxycitronellal, α-amylcinamic aldehyde and 3,5-dimethyl-3-cyclohexene-1-carboxyaldehyde.

11. A perfume-containing resin as claimed in claim 5, wherein the phenol is methyl eugenol.

12. A perfume-containing resin as claimed in claim 5, wherein the ketone is selected from the group consisting of acetophenone, l-carvone, α-damascon, ionone, 4-t-pentylcyclohexanone, 3-amyl-4-acetoxytetrahydropyran, menthone, methylionone, p-t-amylcyclohexanone and acetyl cedrene.

13. A perfume-containing resin as claimed in claim 5, wherein the acetal is phenylacetaldehydedimethyl acetal.

14. A perfume-containing resin as claimed in claim 5, wherein the oxime is 5-methyl-3-heptanon oxime.

* * * * *